US00PP14184P29

(12) United States Plant Patent
Westhoff

(10) Patent No.: US PP14,184 P2
(45) Date of Patent: Sep. 30, 2003

(54) PETUNIA PLANT NAMED 'WESPESORO'

(50) Latin Name: *Petunia×hybrida*
Varietal Denomination: Wespesoro

(75) Inventor: Heinrich Westhoff, Südlohn-Oeding (DE)

(73) Assignee: Josef + Heinrich Westhoff Gartenbau-Spezialkulturen, Sudlohn-Oeding (DE)

( * ) Notice: Subject to any disclaimer, the term of this patent is extended or adjusted under 35 U.S.C. 154(b) by 0 days.

(21) Appl. No.: 10/162,999

(22) Filed: Jun. 5, 2002

(51) Int. Cl.[7] ..... A01H 5/00

(52) U.S. Cl. ..... Plt./356

(58) Field of Search ..... Plt./356

(56) References Cited

PUBLICATIONS

Upov–Rom Plant Variety Database 2002/05, hit on 'Wespesoro' QZ PBR 010178, Apr. 15, 2001.

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Petunia plant named 'Wespesoro', characterized by its cascading plant habit; freely branching habit; dense and bushy growth habit; and single salverform light purple-colored flowers.

1 Drawing Sheet

Botanical classification/cultivar designation: *Petunia×hybrida* cultivar Wespesoro.

BACKGROUND OF THE INVENTION

The present Invention relates to a new and distinct cultivar of Petunia plant, botanically known as *Petunia×hybrida,* and hereinafter referred to by the name 'Wespesoro'.

The new Petunia is a product of a planned breeding program conducted by the Inventor in Sudlohn-Oeding, Germany. The new Petunia originated from a cross-pollination made by the Inventor of a proprietary Petunia selection identified as 98 P 19, not patented, as the female, or seed, parent with a proprietary Petunia selection identified as 98 P 91, not patented, as the male, or pollen, parent. The new Petunia was selected by the Inventor in 1999 in a controlled environment in Sudlohn-Oeding, Germany.

Asexual reproduction of the new cultivar by terminal cuttings taken in Sudlohn-Oeding, Germany since 2000, has shown that the unique features of this new Petunia are stable and reproduced true to type in successive generations.

SUMMARY OF THE INVENTION

Plants of the cultivar Wespesoro have not been observed under all possible environmental conditions. The phenotype may vary somewhat with variations in environment such as temperature and light intensity without, however, any variance in genotype.

The following traits have been repeatedly observed and are determined to be the unique characteristics of 'Wespesoro'. These characteristics in combination distinguish 'Wespesoro' as a new and distinct Petunia cultivar:

1. Cascading plant habit.
2. Freely branching habit.
3. Dense and bushy growth habit.
4. Single salverform light purple-colored flowers.

Plants of the new Petunia have darker green-colored leaves and smaller flowers than plants of the female parent, the selection 98 P 19. Plants of the new Petunia have larger and lighter purple-colored flowers than plants of the male parent, the selection 98 P 91.

Plants of the cultivar Wespesoro can be compared to plants of the Petunia cultivar Surfinia Pink Vein, not patented. However in side-by-side comparisons conducted in Sudlohn-Oeding, Germany, plants of the new Petunia and the cultivar Surfinia Pink Vein differed in the following characteristics:

1. Plants of the new Petunia had narrower stems than plants of the cultivar Surfinia Pink Vein.
2. Plants of the new Petunia had smaller leaves than plants of the cultivar Surfinia Pink Vein.
3. Plants of the new Petunia had larger flowers than plants of the cultivar Surfinia Pink Vein.
4. Flower color of plants of the new Petunia differed slightly from flower color of plants of the cultivar Surfinia Pink Vein.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia.

The photograph at the top of the sheet comprises a side perspective view of a typical plant of 'Wespesoro'.

The photograph at the bottom of the sheet comprises a close-up view of a typical flower and leaves of 'Wespesoro'.

DETAILED BOTANICAL DESCRIPTION

In the following description, color references are made to The Royal Horticultural Society Colour Chart, 1995 Edition, except where general terms of ordinary dictionary significance are used. Plants used for the photographs and the description were grown in 12-cm containers during the spring and summer for about 20 weeks in a glass-covered greenhouse and under conditions which closely approximate commercial production conditions in Sudlohn-Oeding, Germany. During the production of the plants, day temperatures were about 20 to 25° C. and night temperatures were about 16 to 18° C.

Botanical classification: *Petunia×hybrida* cultivar Wespesoro.

Parentage:

*Female parent.*—Proprietary *Petunia×hybrida* selection identified as 98 P 19, not patented.

*Male parent.*—Proprietary *Petunia×hybrida* selection identified as 98 P 91, not patented.

Propagation:

*Type cutting.*—Terminal vegetative cuttings.

*Time to initiate roots.*—About 18 days at 20° C.

*Time to develop roots.*—About 20 to 28 days at 20° C.

*Root description.*—Numerous, fine, fibrous and well-branched.

Plant description:

*Form.*—Annual flowering plant; initially upright, then cascading. Viscid, glandular pubescent. Freely continuous basal branching with lateral branches potentially forming at every node.

*Usage.*—Appropriate for hanging baskets, window boxes and patio containers.

*Plant height* (*from soil level to top of plant plane*).—About 20 cm.

*Plant diameter.*—About 60 cm.

*Stem description.*—Main branches, length: About 77 to 82 cm. Main branches, diameter: About 3.3 mm. Lateral branches, length: About 38 cm. Lateral branches, diameter: About 1.7 mm. Internode length: About 3.3 cm. Texture: Pubescent. Color: 144A.

*Foliage description.*—Arrangement: Before flowering, alternate; after flowering, opposite; simple; sessile. Length: About 3.3 cm. Width: About 1.4 cm. Shape: Lanceolate. Apex: Acute. Base: Attenuate. Margin: Entire. Aspect: Flat. Texture, upper and lower surfaces: Pubescent. Venation pattern: Pinnate. Petiole length: About 1 mm. Petiole diameter: About 1.5 mm. Color: Young and mature foliage, upper surface: 137A. Young and mature foliage, lower surface: 137C. Venation, upper surface: 137C. Venation, lower surface: 144B. Petiole, upper and lower surfaces: 144B.

Flower description:

*Flower type and habit.*—Single salverform flowers; flowers face upward and outward; single, axillary. Flowers persistent. Freely flowering.

*Natural flowering season.*—Long day responsive; flowering from April until frost in the autumn in Germany; flowering continuous during this period.

*Fragrance.*—None detected.

*Flower longevity on the plant.*—About one week.

*Flower size.*—Diameter: About 5.7 cm. Depth (height): About 3.8 cm. Tube length: About 3 cm. Throat diameter, distal end: About 1.2 cm. Tube diameter, proximal end: About 4 mm.

*Flower buds.*—Length: About 4.25 cm. Diameter: About 6 mm. Shape: Linear to oblong. Color: Towards apex, 161C; mid-section, 187B; towards base, 154A.

*Petals.*—Arrangement/appearance: Single whorl of five petals, fused into flared trumpet. Length from throat: About 2.7 cm. Width: About 2.8 cm. Shape: Roughly spatulate. Apex: Obtuse, slightly cuspidate. Margin: Entire. Texture: Smooth, satiny. Color: When opening, upper surface: 65B; towards base, central spots, 64C. When opening, lower surface: 65D; towards base, central spots, 64A. Fully opened, upper and lower surfaces: 65D; towards base, central spots, 64B to 64D. Flower throat (inside): Towards base, 155A; towards apex, 79C. Flower tube (outside): Towards base, 155A; towards apex, 77D. Venation, upper surface: 197A. Venation, lower surface: 144B. Venation, throat: Primary veins, 197A; secondary veins, 79C. Venation, tube: Primary veins, 144B; secondary veins, 77D.

*Sepals.*—Arrangement/appearance: Single whorl of five sepals, fused at base; star-shaped. Length: About 1.9 cm. Width: About 3 mm. Shape: Linear. Apex: Rounded. Margin: Entire. Texture, upper and lower surfaces: Pubescent. Color, upper surface: 137A. Color, lower surface: 137B.

*Peduncles.*—Length: About 3.1 cm. Width: About 1 mm. Strength: Flexible and wiry, holding flowers outwardly. Texture: Pubescent. Color: 144A.

*Reproductive organs.*—Stamens: Quantity: Five per flower. Anther shape: Four-parted, reniform. Anther length: About 2.5 mm. Anther width: About 2 mm. Anther color: 159C. Pollen amount: Moderate to abundant. Pollen color: 158A. Pistils: Quantity: One per flower. Pistil length: About 2.6 cm. Stigma shape: Ovate. Stigma color: 144B to 144C. Style length: About 2 cm. Style color: 144C. Ovary color: 144A to 144B.

*Seed/fruit.*—Seed and fruit production have not been observed.

Disease/pest resistance: Plants of the new Petunia have not been noted to be resistant to pathogens or pests common to Petunia.

Temperature tolerance: Plants of the new Petunia have been observed to be tolerant to temperatures from 2 to 30° C.

It is claimed:

1. A new and distinct cultivar of Petunia plant named 'Wespesoro', as illustrated and described.

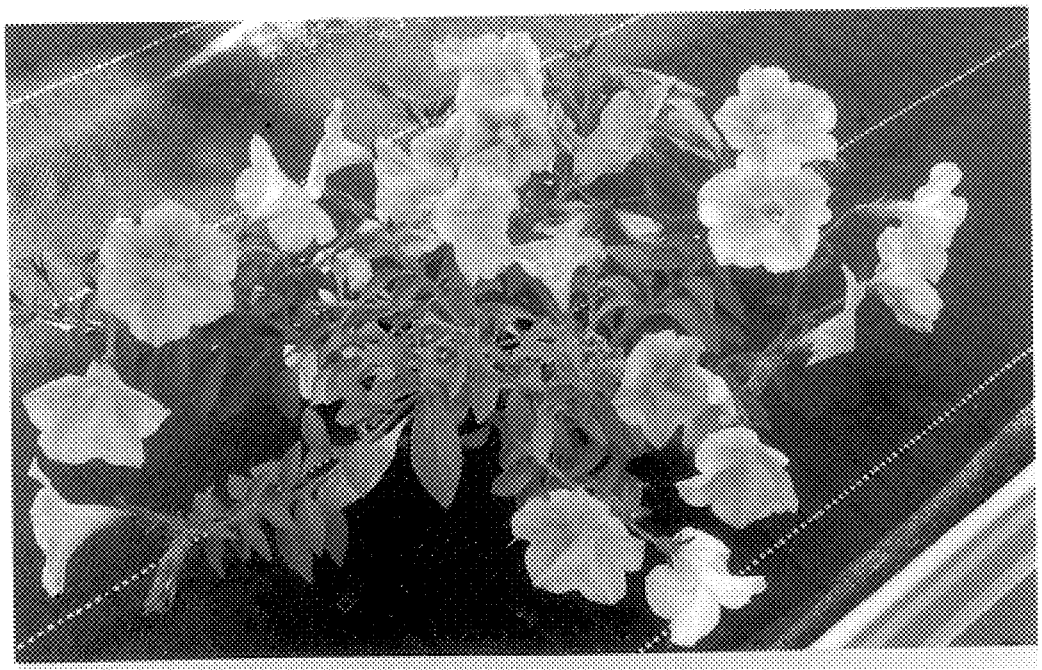
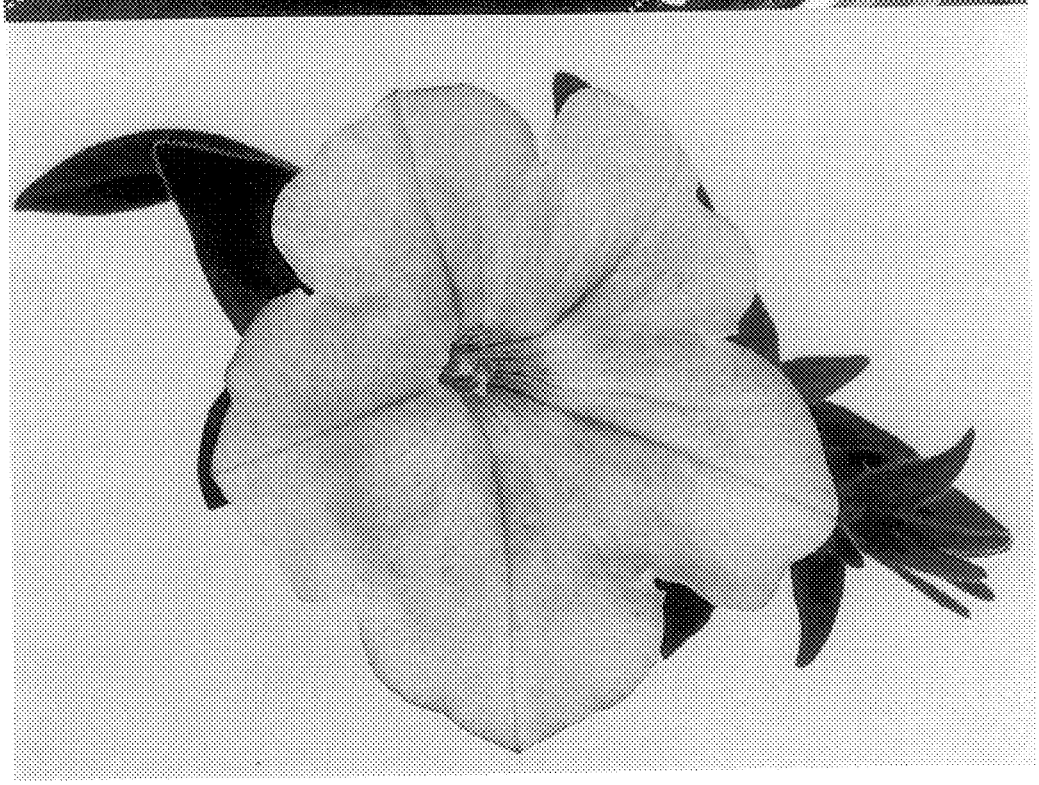

* * * * *